United States Patent [19]

Nelson et al.

[11] Patent Number: 5,071,755

[45] Date of Patent: Dec. 10, 1991

[54] BIODEGRADATION OF ALIPHATIC CHLOROETHYLENE COMPOUNDS

[75] Inventors: Michael J. K. Nelson, Pensacola, Fla.; Al Willis J. Bourquin, Redmond, Wash.; Parmely H. Pritchard, Gulf Breeze, Fla.

[73] Assignees: Ecova Corporation, Redmond, Wash.; The United States of America as represented by the Administrator of the Environmental Protection Agency, Washington, D.C. ; a part interest

[21] Appl. No.: 550,326

[22] Filed: Jul. 9, 1990

Related U.S. Application Data

[63] Continuation of Ser. No. 44,213, Apr. 13, 1987, Pat. No. 4,959,315.

[51] Int. Cl.$^5$ .......................... C02F 3/34; C12N 1/28; C12P 5/02
[52] U.S. Cl. .................................... 435/167; 435/168; 435/170; 435/262; 435/877
[58] Field of Search ............... 435/167, 168, 170, 262, 435/877

[56] References Cited

U.S. PATENT DOCUMENTS

| | | | |
|---|---|---|---|
| 3,979,283 | 9/1976 | Prudom .............................. | 435/167 |
| 3,980,557 | 9/1976 | Yall et al. ........................... | 435/167 |
| 4,452,894 | 6/1984 | Olsen et al. ........................ | 435/167 |
| 4,477,570 | 10/1984 | Coloruotolo et al. ............. | 435/167 |
| 4,664,805 | 5/1987 | Focht ................................. | 435/167 |
| 4,713,343 | 12/1987 | Wilson, Jr. et al. ............... | 435/167 |
| 4,925,802 | 5/1990 | Nelson et al. ...................... | 435/167 |

OTHER PUBLICATIONS

Nelson et al., "Isolation of a Pure Culture that Metabolizes Trichloroethylene", Abstract 86th Am. Mtg. of Am. Soc. Micr., Mar. 23-28, 1986.

Subramanian et al. & Biol. Chem. 260(4):2355-63 (1985).

Nelson, Michael J. K. et al., "Biodegradation of Trichloroethylene and Involvement of an Aromatic Biodegradative Pathway", Applied and Environmental Microbiology 53(5), 949-954, May 1987.

Nelson, Michael J. K. et al., "Aerobic Metabolism of Trichloroethylene by a Bacterial Isolate", Applied and Environmental Microbiology 52(2), 383-384, Aug. 1986.

*Primary Examiner*—Douglas W. Robinson
*Assistant Examiner*—J. Witz
*Attorney, Agent, or Firm*—Christenson, O'Connor, Johnson & Kindness

[57] ABSTRACT

A method of degrading halogenated aliphatic hydrocarbons is disclosed comprising incubating microorganisms capable of degrading halogenated aliphatic hydrocarbons by an aromatic degradative pathway together with the halogenated aliphatic hydrocarbons under conditions such that said aromatic degradative pathway is active.

2 Claims, No Drawings

BIODEGRADATION OF ALIPHATIC CHLOROETHYLENE COMPOUNDS

This invention was made with Government support under Contract No. 68-03-6265 awarded by the U.S. Environmental Protection Agency. The Government has certain rights in the invention.

This application is a continuation of Ser. No. 07/044,213, filed Apr. 30, 1987, now U.S. Pat. No. 4,959,315.

BACKGROUND OF THE INVENTION

1. Technical Field

The present invention relates, in general, to the biodegradation of halogenated aliphatic hydrocarbons, and in particular, to the biodegradation of trichloroethylene.

2. Background Information

The halogenated aliphatic hydrocarbon trichloroethylene (TCE) is a volatile, chlorinated compound of increasing concern as a groundwater contaminate. TCE is potentially carcinogenic and is resistant to biological or abiological decomposition in subsurface waters. Conventional water treatment processes have been found to be ineffective in removing TCE from ground-water. Results obtained with aeration and adsorption to granular activitied charcoal or Ambersorb resin, however, are more encouraging.

The TCE degradation potential of microbes found in groundwater systems has been examined. Evidence of anaerobic biodegradation has been reported, but the products of degradation include equally harmful metabolites, such as dichloroethylenes and vinyl chloride. Several studies suggest that TCE may be degraded under methanogenic conditions. Complete mineralization of TCE was obtained when nonsterile solids were exposed to natural gas in air, suggesting that methanotrophic microorganisms are capable of degrading TCE. A possible mechanism for the degradation of TCE by methanotrophs involves epoxidation of TCE by methane monooxygenase followed by transport of the epoxide out of the cell. In the aqueous extracellular environment, the TCE epoxide would be subject to rapid rearrangment yielding dichloroacetic acid, formate, and carbon monoxide, each of which would then be further degraded. All reports of TCE metabolism have involved the use of undefined, mixed populations of microorganisms. No pure cultures of methanotrophs have been reported to degrade TCE.

It is an object of the present invention to provide a method for the biodegradation of halogenated aliphatic hydrocarbons.

It is another object of the invention to provide a method for the complete mineralization of halogenated aliphatic hydrocarbons.

It is a further object of the invention to provide a process for isolating microorganisms capable of degrading halogenated aliphatic hydrocarbons.

It is another object of the invention to provide pure cultures of microorganisms capable of degrading halogenated aliphatic hydrocarbons.

Further objects and advantages of the present invention will be apparent from the discussion which follows.

SUMMARY OF THE INVENTION

The invention relates to a method of degrading halogenated aliphatic hydrocarbons. The method comprises incubating microorganisms capable of degrading halogenated aliphatic hydrocarbons by an aromatic degradative pathway, together with halogenated aliphatic hydrocarbons under conditions such that the aromatic degradative pathway is active. The method results in the conversion of the halogenated aliphatic hydrocarbons into non-toxic products, including carbon dioxide and inorganic chloride.

The method is useful in decontaminating halogenated aliphatic hydrocarbon-polluted environments. Decontaminating systems can utilize pure cultures of microorganisms capable of degrading halogenated aliphatic hydrocarbons in continuous-flow bioreactor-type systems. Also, natural microbial communities can be stimulated to degrade halogenated aliphatic hydrocarbons by addition to the contaminated site of an amount of an aromatic inducer sufficient to induce the degradation of the halogenated alphatic hydrocarbons; the inducer being a compound capable of inducing an aromatic degradative pathway by which halogenated aliphatic hydrocarbons are degraded.

Strains of microorganisms can be derived, either by selection, mutation, or recombinant techniques, that will degrade halogenated aliphatic hydrocarbons with or without the addition of aromatic inducers.

DETAILED DESCRIPTION OF THE INVENTION

According to the present invention there is provided a method of degrading halogenated aliphatic hydrocarbons. The method comprises incubating microorganisms capable of degrading halogenated aliphatic hydrocarbons by an aromatic degradative pathway, together with the halogenated aliphatic hydrocarbon under conditions such that the aromatic degradative pathway is active. Halogenated aliphatic hydrocarbons subject to degradation by the process of the present invention include, but are not limited to, chlorinated aliphatic hydrocarbons. Chlorinated aliphatic hydrocarbons which can be degraded by the process of the present invention include chloroethanes and chloroethylenes, for example, trichloroethylene, 1,1-dichloroethylene, cis-1,2-dichloroethylene, and chloroethylene (vinyl chloride).

The microorganisms used in the above-described process are selected, mutated, or genetically engineered to degrade halogenated aliphatic hydrocarbons by an aromatic degradative pathway.

Microorganisms capable of degrading halogenated aliphatic hydrocarbons can be selected from mixed cultures by growing the culture in the presence of an amount of an aromatic compound capable of inducing halogenated aliphatic hydrocarbon degradation, under conditions such that the culture is enriched for microorganisms capable of degrading halogenated aliphatic hydrocarbons. Pure cultures of such microorganisms can then be isolated by subculturing the enriched population using known techniques. More specifically, microorganisms can be isolated as follows. Samples are taken from the natural flora. A halogenated aliphatic hydrocarbon, in the presence or absence of an aromatic compound capable of inducing an aromatic degrative pathway by which halogenated aliphatic hydrocarbons are degraded, is added to each sample. Each sample is then analyzed for halogenated aliphatic hydrocarbon degradation compared to sterile controls. For each sample showing significant halogenated aliphatic hydrocarbon degradation, aliquots of the sample are plated onto agar plates. Colonies of the microorganisms are grown and each is tested for its ability to degrade halogenated aliphatic hydrocarbons, in the presence or absence of an aromatic compound capable of inducing an aromatic degrative pathway by which halogenated aliphatic hydrocarbons are degraded.

In one embodiment of the present invention, a pure culture can be used. For example, G4 (deposited at the American Type Culture Collection, Rockville, Md., on Apr. 30, 1987) was isolated and used as follows. A water sample from a holding pond at an industrial waste treatment facility for the Naval Air Station (NAS) in Pensacola, Fla., having a history of contamination with organochlorine compounds, was screened for possible TCE degradation. The sample was supplemented with concentrated stock solutions to yield a basal salts medium (J. Gen. Microbiol. (1966) 43: 159-271), and 5 ml aliquots were dispensed into 30-ml screw-cap culture tubes (18 by 150 mm). Tubes were sealed with Teflon-faced neoprene rubber septa secured by hole caps to allow access by syringe, TCE (50 nmol) was added as an aqueous stock by syringe through the septum of each tube. Samples (20 µl) of the headspace from each tube were analyzed periodically by gas chromatography for changes in TCE concentration. The injector, oven, and detector temperatures on the gas chromatograph were 100°, 60°, and 325° C., respectively. The carrier gas was $H_2$ (1 ml/min) and the makeup gas was 90% argon-10% methane (45 ml/min through the detector).

The sample caused a substantial decrease in TCE concentration as compared to autoclaved controls. Subcultures of this sample metabolized TCE when filter-sterilized or autoclaved water from the original sampling site (NAS water) was used to make up the basal salts medium for the experiments. NAS water was therefore used in the medium for all subsequent tests for TCE metabolism. Aliquots of the sample were plated on glucose medium (10 mM glucose, 0.05% yeast extract in basal salts medium) for isolation of colonies. Resulting isolates were grown in glucose medium to stationary phase, and 1-ml portions were added to 50-ml Wheaton serum vials containing NAS medium (10 ml of basal salts solution made up in NAS water and supplemented with 0.05% yeast extract). The vials were sealed with Teflon-faced neoprene serum stoppers and crimp caps, and TCE (50 nmol) was added as an aqueous stock by syringe through the septa. Changes in TCE concentrations in the medium after equilibration with the headspace of the vials were determined by extracting 1.5-ml samples with an equal volume of n-pentane and injecting 1.5 µl of the extract into the gas chromatograph under the conditions described above. All subsequent experiments also followed this method for monitoring TCE metabolism. In this manner, a pure culture, designated strain G4, which degraded TCE was obtained.

Strain G4 is a nonmotile, gram-negative, rod-shaped bacterium which grows predominately in pairs and short chains in logarithmic phase. The isolate is oxidase negative, catalase positive, resistant to ampicillin and carbenicillin (greater than 100 and 1,000 µg/ml, respectively), and is strictly aerobic; the isolate has no specific growth requirements. Based on these criteria, G4 may be ascribed to the genus Acinetobacter.

Although strain G4 grows on a variety of substrates, including glucose, lactate, succinate, acetate, and ethanol, no growth is observed with methane (up to 50% of the culture headspace) or methanol.

Additional strains capable of degrading halogenated aliphatic hydrocarbons by an aromatic degradative pathway can be isolated from the natural flora using a technique comparable to that used to isolate G4 except that, instead of waste water, one of the below-described aromatic inducers can be added to the medium in an inducing amount.

In the method of the present invention, microorganisms selected for their ability to degrade halogenated aliphatic hydrocarbons by induction with aromatic compounds, can be induced prior to being incubated with the halogenated aliphatic hydrocarbon to be degraded. Alternatively, the microorganisms can be induced with the aromatic hydrocarbon at the same time the microorganisms are incubated with the halogenated aliphatic hydrocarbon to be degraded. The latter would be the case when (a) aromatic inducers are added to natural flora at halogenated aliphatic hydrocarbon-contaminated sites, or when (b) microorganisms and aromatic inducers are each individually added to halogenated aliphatic hydrocarbon-contaminated site.

In the method of the present invention, aromatic compounds used to induce metabolic pathways by which halogenated aliphatic hydrocarbons are degraded include compounds capable of inducing a meta fission pathway in the microorganisms, for example, substituted benzenes, advantageously, phenol, toluene, o-cresol, and m-cresol.

The invention also relates to cultures of microorganisms selected, mutagenized, or genetically engineered to degrade halogenated aliphatic hydrocarbons by an aromatic degradative pathway. The microorganisms may be present as a pure culture.

The process of the present invention is useful in decontaminating halogenated aliphatic hydrocarbon-polluted environments using enriched or pure cultures of microorganisms capable of degrading halogenated aliphatic hydrocarbons by an aromatic degradative pathway, in a continuous-flow bioreactor-type system. Alternatively, it is anticipated that natural flora will be stimulated to degrade halogenated aliphatic hydrocarbons by an aromatic degradative pathway, by adding to the halogenated aliphatic hydrocarbon-contaminated environment, an amount of an aromatic inducer sufficient to induce halogenated aliphatic hydrocarbon degradation; the inducer being capable of inducing aromatic degradative pathways by which halogenated aliphatic hydrocarbons are degraded.

The invention is illustrated by way of the following non-limiting examples:

EXPERIMENTAL CONDITIONS AND EXAMPLES

Culture conditions. All media contained basal salts (MSB [J. Gen. Microbiol. (1966) 43: 159-271]), and cultures were grown at 30° C. with shaking (200 rpm). Cultures were maintained on 10 mM glucose.

Induced cultures of strain G4 were grown from a 5% inoculum on 20 mM sodium lactate-2 mM inducer for 20 h; an additional amount of 2 mM inducer was added at 16 h. Unless otherwise indicated, cells were harvested by centrifugation and resuspended in MSB to 1/20 the original volume and 0.1 ml (ca. $7 \times 10^9$ CFU) was used as the inoculum for the experiments.

TCE degradation experiments. TCE degradation experiments were similar to those described by Nelson et al. (Appl. Environ. Microbiol. (1986) 52: 383-384) and used 50 ml serum bottles sealed with butyl rubber stoppers and crimp caps. Each bottle contained 10 ml of MSB, TCE, and inoculum as described below. Unless otherwise indicated, experiments were terminated after 24 h of incubation at 26° C. TCE degradation was monitored by measuring TCE concentrations in the aqueous phase of the test bottles by pentane extraction and gas chromatography (see Nelson et al (1986) cited above). TCE in solution does not equal total TCE in experiments because of its partitioning between the liquid and gas phases of the test bottles. However, dissolved TCE is proportional to total TCE added and thus serves as a reliable method of monitoring. No TCE remained in the gas phase when it was below detection limits in the aqueous phase.

Chloride analysis. Chloride was determined with a model 94-17B chloride-specific electrode and a model 90-02 reference electrode calibrated with KCl standards made up in 0.1M potassium phosphate buffer (pH 7.0) (P7 buffer). Alternatively, chloride ion concentration was determined spectrophotometrically (Chem. Soc. Japan (1956) 29: 860–864). Experiments to detect the production of chloride were performed like TCE degradation experiments and contained 200 nmol of TCE and 1 mM phenol. P7 buffer replaced MSB, and phenol-induced, resuspended cultures of strain G4 were used as the inoculum. Results were corrected for background chloride. Time Source experiments were performed by setting up replicate bottles and sacrificing bottles at various times.

Tests for catechol ring fission pathways. The production of β-ketoadipate from catechol, as determined by the method of Rothera (Proc. Biochem. Soc. (1948) 43: 5–6; J. Physiol. (London) (1908) 248: 491–494.), was used as a test for the presence of a catechol ortho ring fission pathway. Cultures of strain G4 induced with phenol, toluene, or benzoate were grown and concentrated as described above. A 0.2 ml sample of each concentrated cell suspension was added to 2.0 ml of 20 mM Tris chloride buffer (pH 8.0), followed by the addition of 3 drops of toluene to solubilize cellular membranes. Catechol (0.2 ml of a 1.0M solution) was added as the ring fission substrate. After 25 min of incubation at 30° C., ca. 3 g of ammonium sulfate and 3 drops of 5% sodium nitroprusside were added. The resulting mixture was overlaid with 1 ml of concentrated (ca. 14M) ammonium hydroxide. A positive test for β-ketoadipate was the production of a purple band at the interface of the layers.

The production of the yellow product, α-hydroxymuconic semialdehyde, from catechol was used as a test for the presence of a catechol meta ring fission pathway. Cells were grown overnight on agar plates containing 20 mM sodium lactate and then exposed to phenol or toluene vapors for 6 h to induce the aromatic degradative pathways. Exposure was achieved by taping to the plate lids cotton-stoppered Durham test tubes containing liquified phenol or toluene. Benzoate induction was accomplished by overnight growth on agar plates containing 10 mM sodium benzoate as the sole carbon source. After induction, cells were sprayed with a 0.1M aqueous solution of catechol. Cells induced for meta ring fission turned bright yellow within 15 min.

Enzyme assays. Catechol-1,2-dioxygenase (C120) and catechol-2,3-dioxygenase (C230) were determined spectrophotometrically at 260 and 375 nm, respectively (Methods in Microbiol. (1977) 6B: 463–478.). Cell extracts were obtained from cells grown with phenol, toluene, or sodium benzoate as the inducer. The cell pellets were suspended in a minimum volume of P7 buffer (ca. 1 ml/g [wet weight] of cells) and disrupted by three passages through a French pressure cell at 138 MPa (20,000 lb/in$^2$). Unbroken cells and debris were separated from the cell extracts by centrifugation for 20 min at 27,000×g.

Protein determinations. Protein was assayed by the method of Bradford (Anal. Biochem. (1976) 72: 248–254) with bovine serum albumin as the standard. Whole cells were preincubated for 15 min in 0.1M NaOH prior to the protein assay.

EXAMPLE 1

Induction of TCE degradation by aromatic compounds

Two hundred nmol of TCE and 1 ml of a latelog-phase culture (ca. 3×10$^9$ CFU) of strain G4 grown on 20 mM lactate were used. Data are the means±standard deviations of triplicate experiments.

The data in Table 1 demonstrate that toluene, o-cresol, and m-cresol stimulated TCE degradation; m-xylene, sodium benzoate, and p-cresol did not stimulate TCE degradation. All of the above-listed compounds, with the exception of m-xylene, were growth substrates for strain G4.

TABLE 1

| Compound added (1mM) | TCE remaining[a] (μM) |
|---|---|
| None | 3.35 ± 0.26 |
| Phenol | 0.04 ± 0.0 |
| Toluene | <0.02[b] |
| m-Xylene | 3.92 ± 0.08 |
| Sodium benzoate | 4.17 ± 0.29 |
| o-Cresol | <0.02 |
| m-Cresol | 0.07 ± 0.09 |
| p-Cresol | 4.04 ± 0.45 |

[a]After 24 h of incubation. A typical control with a sterile inoculum contained 3.5 μM TCE.
[b]Minimum detectable level.

EXAMPLE 2

Production of inorganic chloride by TCE degrading microorganism

When TCE was degraded by strain G4, stoichiometric amounts of inorganic chloride were produced. In two separate sets of experiments (three replicates each), 541±20 and 586±34 nmol of chloride were produced from 200 nmol of TCE, equal to 2.7 and 2.9 chloride ions per TCE molecule, respectively. Time course studies indicated that chloride was produced at a linear rate of 3.6 nmol/min (r=0.96), corresponding to the consumption of 1.2 nmol of TCE per min (assuming three chloride ions per TCE molecule). Complete dechlorination occurred in 3 h; no further Cl$^-$ production was detectable after 5 h.

EXAMPLE 3

Induction of meta fission pathway in TCE degrading microorganism

Aerobic degradation of toluene, phenol, and benzoate produces catechols which are then cleaved by either ortho or meta fission. Strain G4 induced with either toluene or phenol produced a yellow color when sprayed with catechol, indicative of meta fission. The presence of a meta fission pathway in phenol-induced cells was confirmed by spectral analysis of the products of both catechol and 3-methylcatechol. Benzoate-induced cells did not produce a yellow color when sprayed with catechol. However, benzoate-induced cells that were subsequently exposed to either 1 mM toluene or 1 mM phenol for 30 min produced the yellow color from catechol, indicating that the meta fission pathway was still inducible after exposure to benzoate.

A strong positive reaction was obtained when benzoate-induced cells were tested for the production of β-ketoadipate from catechol, indicative of ortho fission. A weak positive reaction was obtained with phenol- and toluene-induced cells, indicating that some ortho fission occurred under these conditions.

Enzyme assays of cell extracts were consistent with the results obtained with whole cells. Phenol- and toluene-induced cells contained C230-specific activities that were over 20-fold higher than the respective C120-specific activities (Table 2). The C230 activities induced with both of these compounds were well over 100-fold higher than the C230 activity for ring fission in benzoate-induced cells. Therefore, strain G4 appears to utilize the ortho fission pathway for benzoate degradation and the meta fission pathway for phenol and toluene degradation.

Thus, aerobic degradation of TCE by strain G4 is associated with a specific aromatic degradative pathway that utilized meta fission.

TABLE 2

C120 and C230 activities of strain G4 induced with phenol, toluene, or benzoate (cells grown)

| Inducer | Activity (μmol/min per mg of protein of: |  |
|---|---|---|
|  | C120 | C230 |
| Phenol | 0.071 | 1.68 |
| Toluene | 0.044 | 1.14 |
| Benzoate | 0.095 | 0.008 |

Cultures were grown on lactate with the indicated compound added as an inducer. Data are the means of two experiments.

EXAMPLE 4

Transformation of other chloro-aliphatics by strain G4

Strain G4 was tested for the ability to transform a variety of chloroethylenes based on the release of chloride from the compounds (Table 3). 1,1-Dichloroethylene, cis-1,2-dichloroethylene and vinyl chloride appeared to be transformed with the release of about one $Cl^-$ per molecule.

TABLE 3

Test of Strain G4 For The Ability To Dechlorinate Chloroethylenes.

| Compound | Chloride Produced[a] (nmol) | Chloride Per Molecule | Percentage Theoretical |
|---|---|---|---|
| 1,1-Dichloroethylene | 445 ± 93 | 1.5 | 74 |
| cis-1,2-Dichloroethylene | 344 ± 153 | 1.2 | 57 |
| Vinyl chloride | 505 ± 43[b] | 0.8 | 84 |
| trans-1,2-Dichloroethylene | 67 ± 51 | 0.2 | 11 |
| 1,1-Dichloroethane | −127 ± 34 | −0.4 | −21 |
| 1,2-Dichloroethane | 9 ± 128 | 0.2 | 1 |
| 1,1,1-Trichloroethane | −16 ± 138 | −0.1 | −3 |
| 1,1,2-Trichloroethane | −153 ± 26 | −0.8 | −26 |
| 1,1,2,2-Tetrachloroethane | 89 ± 26 | 0.6 | 15 |
| Tetrachloroethylene | −46 ± 105 | −0.3 | −8 |

[a]Background subtracted. Data are the means and standard deviations from three replicates. The compounds were added to yield 600 nmol of chloride-equivalents.
[b]Determined spectrophotometrically (Chem. Soc. Japan (1956) 29: 860-864).

EXAMPLE 5

Other microorganisms tested for the ability to metabolize TCE

Several strains of bacteria capable of degrading various aromatic compounds were tested for the ability to metabolize TCE in the presence of their respective aromatic substrates (Table 4). Under the conditions tested, only two toluene-utilizers P. putida strain F1 (Biochemistry (1968) 7:2653–2662) and strain B5 (isolated using similar techniques) were capable of completely metabolizing TCE. These two strains degraded toluene via 3-methylcatechol. Another toluene-utilizer, P. putida strain mt-2, did not metabolize TCE. This organism degrades toluene via oxidation of the methyl group to form benzoate and subsequent dioxygenation to form catechol. Two mutants of P. putida strain F1, defective in the toluene degradative pathway, were tested for the ability to metabolize TCE (Table 5). The mutant Pp106 lacking the first enzyme of the pathway, toluene-2,3-dioxygenase, did not show any substantial metabolism of TCE, although another mutant, Pp39D, lacking the next enzyme in the pathway, the dihydrodiol dehydrogenase, metabolized TCE as effectively as the parent strain.

TABLE 4

TCE Metabolism By Microorganisms That Degrade Aromatic Compounds[a]

| Organism | Aromatic Substrate | TCE Remaining (nmol) |
|---|---|---|
| P. putida NCIB 9816 | Naphthalene | 0.81 ± 0.06 |
| Beijerinkia sp. | Biphenyl | 0.66 ± 0.12 |
| P. putida strain mt-2 | Toluene | 0.75 ± 0.17 |
| P. putida strain B5 | Toluene | <0.02 |
| P. putida strain F1 | Toluene | <0.02 |
| None | None | 0.63 ± 0.02 |

[a]Cultures used for inoculum were grown overnight on 10 mM glucose medium and 1 ml of each was used as inoculum. The indicated aromatic substrates were included in the TCE metabolism experiments at 1 mM. At initiation of the experiments, 50 nmol TCE was added and samples were incubated for 24 hours.

TABLE 5

Metabolism of TCE by Mutants of P. putida F1 Unable to Degrade Toluene[a]

| Strain | Defective Enzyme | TCE remaining (nmol) |
|---|---|---|
| Parent strain | None | <0.02 |
| Pp 106 | Toluene dioxygenase | 2.98 ± 0.09 |
| Pp 39D | Dihydrodiol dehydrogenase | <0.02 |
| None | — | 3.84 ± 0.13 |

[a]Toluene at 1 mM replaced phenol in these TCE metabolism experiments.

The foregoing invention has been described in some detail by way of examples for purposes of clarity and understanding. Various combinations in form and detail can be made without departing from the scope of the invention.

What is claimed is:

1. A method of degrading an aliphatic chloroethylene compound comprising incubating aid aliphatic chloroethylene compound with microorganisms capable of expressing an oxygenase enzyme from an aromatic degradative meta ring fission pathway in the absence of an aromatic compound capable of inducing said pathway, wherein said aliphatic chloroethylene compound is degraded by said microorganisms.

2. The method of claim 1 wherein said microorganisms are selected, mutated or genetically engineered to express said oxygenase enzyme.

* * * * *

UNITED STATES PATENT AND TRADEMARK OFFICE
CERTIFICATE OF CORRECTION

PATENT NO. : 5,071,755
DATED : December 10, 1991
INVENTOR(S) : M.J.K. Nelson et al.

It is certified that error appears in the above-identified patent and that said Letters Patent is hereby corrected as shown below:

| COLUMN | LINE | | |
|---|---|---|---|
| [56] | Firm | "O'3 Connor" should be --O'Connor-- |
| [56] | Publications | "86th Am. Mtg." should be --86th Ann. Mtg.-- |
| 8 | 58 | "aid" should be --said-- |

Signed and Sealed this

Fourth Day of May, 1993

Attest:

MICHAEL K. KIRK

Attesting Officer     Acting Commissioner of Patents and Trademarks